(12) United States Patent
Rao et al.

(10) Patent No.: US 10,392,364 B2
(45) Date of Patent: Aug. 27, 2019

(54) PROCESS FOR SYNTHESIS OF LENALIDOMIDE

(71) Applicant: AVRA LABORATORIES PVT. LTD., Hyderabad (IN)

(72) Inventors: Ramakrishna Rao, Hyderabad (IN); Ramadevi Nandipati, Hyderabad (IN); Ravi Gooda, Hyderabad (IN); Mukesh Padmakar Shewalkar, Hyderabad (IN); Venkat Vasantrao Bhadke, Hyderabad (IN)

(73) Assignee: AVRA LABORATORIES PVT. LTD., Hyderabad (IN)

( * ) Notice: Subject to any disclaimer, the term of this patent is extended or adjusted under 35 U.S.C. 154(b) by 168 days.

(21) Appl. No.: 15/520,980

(22) PCT Filed: Aug. 11, 2015

(86) PCT No.: PCT/IN2015/000318
§ 371 (c)(1),
(2) Date: Apr. 21, 2017

(87) PCT Pub. No.: WO2016/024286
PCT Pub. Date: Feb. 18, 2016

(65) Prior Publication Data
US 2018/0334443 A1    Nov. 22, 2018

(30) Foreign Application Priority Data
Aug. 11, 2014 (IN) .............. 3938/CHE/2014

(51) Int. Cl.
C07D 401/04 (2006.01)

(52) U.S. Cl.
CPC ........ C07D 401/04 (2013.01); *C07B 2200/13* (2013.01)

(58) Field of Classification Search
CPC ................................................... C07D 401/04
USPC ...................................................... 546/201
See application file for complete search history.

(56) References Cited

U.S. PATENT DOCUMENTS

| 5,635,517 | A | 6/1997 | Muller et al. |
| 7,465,800 | B2 | 12/2008 | Jaworsky |
| 8,877,932 | B2 | 11/2014 | Konakanchi |
| 2012/0071509 | A1 | 3/2012 | Gore |
| 2012/0184746 | A1 | 7/2012 | Kapoor et al. |
| 2014/0121245 | A1 | 5/2014 | Konakanchi et al. |

FOREIGN PATENT DOCUMENTS

| CN | 103601717 A | 2/2014 |
| IN | IN47CHE2006 | 1/2007 |
| WO | 2005/023192 A2 | 3/2005 |
| WO | 2006/028964 A1 | 3/2006 |
| WO | 2009/114601 A2 | 9/2009 |
| WO | 2010/100476 A2 | 9/2010 |
| WO | 2010/129636 A2 | 11/2010 |
| WO | 2011/061611 A1 | 5/2011 |

*Primary Examiner* — Patricia L Morris
(74) *Attorney, Agent, or Firm* — Kramer Amado, P.C.

(57) ABSTRACT

Disclosed herein is an improved process for preparation of Lenalidomide and crystalline polymorphic forms thereof.

4 Claims, 2 Drawing Sheets

PROCESS FOR SYNTHESIS OF LENALIDOMIDE

TECHNICAL FIELD OF THE INVENTION

The present invention relates to an improved process for preparation of Lenalidomide and-crystalline polymorphic forms thereof.

BACKGROUND AND PRIOR ART

Lenalidomide chemically known as 3-(4-amino-1-oxoisoindolin-2-yl)piperidine-2,6-dione is a non-polypeptide compound which decrease the levels of TNF [alpha]. It was approved by US FDA in 2005 for the patients and it is commercially sold as REVLIMID™ by Celgene.

TNF[alpha] is a candidate inducing angiogenesis in inflammation, wound repair, and tumor growth. TNF [alpha] production also has been associated with cancerous conditions, particularly induced tumors. It also plays a role in the area of chronic pulmonary inflammatory diseases. The deposition of silica particles leads to silicosis, a disease of progressive respiratory failure caused by a fibrocystic reaction. Lenalidomide inhibits tumor angiogenesis, tumor secreted cytokines and tumor proliferation through the induction of apoptosis. Lenalidomide has also shown efficacy in the class of hematological disorders known as myelodysplastic syndromes (MDS).

Lenalidomide and its process are disclosed in U.S. Pat. No. 5,635,517. The process for synthesis of Lenalidomide includes reacting methyl 2-bromomethyl-3-nitrobenzoate with 2,6 dioxopiperidin-3-ammonium chloride in presence of DMF and triethylamine to obtain 3-(4-nitro-1-oxo-1,3-dihydroisoindol-2-yl)-piepridine-2,6-dione and hydrogenating the nitro intermediate, 3-(1-oxo-4-nitro-1,3-dihydro-isoindol-2-yl)-piperidine-2,6-dione, at 50 psi pressure using 10% Pd/C catalyst in 1,4-dioxane. The residue is crystallized from ethyl acetate and further from dioxane/ethyl acetate mixture to yield about 36% of the product.

WO2006/028964 describes the preparation of Lenalidomide which involves the preparation of the nitro intermediate comprising coupling of an L-glutamine methyl ester with methyl-2-bromomethyl-3-nitro benzoate in acetonitrile and cyclising the resultant N-(1-oxo-4-nitro-isoindol-2-yl)-L-glutamine methyl ester. The nitro intermediate is then reduced with Pd/C in methanol followed by cyclisation under acidic conditions to yield 51% of Lenalidomide.

PCT publication No. WO 2009/114601 discloses improved processes for the preparation of substantially pure Lenalidomide. According to the publication, Lenalidomide can be prepared by reacting methyl 2-halomethyl-3-nitrobenzoate with α-amino glutarimide hydrochloride in the presence of triethylamine and N-methylpyrrolidone (NMP) or acetonitrile solvent to obtain 3-(4-nitro-1-oxo-1,3-dihydroisoindol-2-yl)-piepridine-2,6-dione and then hydrogenating with palladium carbon in presence of a solvent selected from alcohols, ketonic solvents, DMF, DMSO, DMAc and an acid selected from inorganic and organic acids.

Indian Application No. 047/CHE/2006 which was published on Nov. 23, 2007, discloses a process which comprises hydrogenating 3-(4-nitro-1-oxo-1,3-dihydroisoindol-2-yl)-piperidine-2,6-dione using 10% Pd on carbon in a mixture of solvents comprising methanol and N,N-dimethylformamide to provide Lenalidomide.

PCT Publication No. WO 2010/100476 ('476 patent) discloses a process for the preparation of Lenalidomide. According to the publication, Lenalidomide can be prepared by catalytic reduction of 3-(1-oxo-4-nitro-1,3-dihydro-isoindol-2-yl)-piepridine-2,6-dione with palladium carbon preferably in acetonitrile and methanol. WO '476 also discloses a process for the preparation of 3-(1-oxo-4-nitro-1,3-dihydro-isoindol-2-yl)-piperidine-2,6-dione by reacting 3-amino-piperidine-2,6-dione hydrochloride with methyl 2-bromomethyl-3-nitro-benzoate in N,N-dimethylformamide.

The prior art processes suffer from the following disadvantages; viz. (i) low yield of the product; (ii) low yield of the nitro intermediate and (iii) in the use of large amount of solvents that makes the processes commercially not viable.

Further, various polymorphic forms of 3-(4-amino-1-oxoisoindolin-2-yl)piperidine-2,6-dione (generically known as Lenalidomide) are mentioned in PCT publication WO2005/023192. Polymorphic forms viz. Form A in anhydrous form with no water content, Form B as hemihydrate with moisture content 3.1%, Form C as hemisolvate of acetone, Form D solvated with water and acetonitrile. Further, Form E is a dehydrate with moisture content of 11.8%, Form F is an unsolvated material obtained by complete dehydration of Form E, Form G is an unsolvated form obtained by slurrying Form B and Form E in THF Form H is a crystalline solid hydrated with 0.25 moles of water.

Further, WO2005/023192 discloses the hemihydrate Form B obtained by crystallization from many solvents, including, but not limited to hexane, toluene and water. It is further described that Form B is the desired polymorphic form for active pharmaceutical ingredient (API).

US2014/0121245 relates to anhydrous polymorphic Form I of Lenalidomide. The synthetic process for Lenalidomide comprises side chain bromination of methyl 2-methyl-3-nitro-benzoate with NBS in suitable solvents selected from halogenated hydrocarbons; alkylation followed by cyclisation of methyl 2-bromomethyl-3-nitro-benzoate with d1,3-Aminoglutarimide in solvents such as dimethylformamide, methanol, ethanol, acetonitrile to obtain 3-(4-nitro-1-oxo-1, 3dihydro-isoindol-2-yl)-piperidine-2,6-dione; catalytic hydrogenation of 3-(4-nitro-1-oxo-1,3dihydro-isoindol-2-yl)-piperidine-2,6-dione in solvents such as dimethylformamide, methanol, ethanol, isopropyl alcohol or mixture of these solvents to obtain Lenalidomide polymorphic Form I.

In the alternate synthesis disclosed in US'245, Form-I is obtained by suspending the wet Lenalidomide cake, which is obtained directly after filtration of the catalyst from the reaction mass, in solvents such as isopropyl alcohol, dimethylformamide and acetonitrile followed by reducing or completely distilling the solvents at temperatures varying 65° C. to 110° C. under vacuum or without vacuum and then finally drying at temperature varying from 40-110° C. either under vacuum or without vacuum. Also, the anhydrous polymorphic Form-I of Lenalidomide is obtained by filtration and drying at temperature varying from 40-110° C. either under vacuum or without vacuum after azeotropically distilling the solvent toluene completely or partially with or without vacuum, at temperatures varying 65° C. to 110° C.

US'245 further reports that anhydrous polymorphic Form I of Lenalidomide can also be prepared by taking the hydrated Form B or Form E of Lenalidomide in a solvent such as isopropyl alcohol or in acetonitrile. The polymorphic Form I of Lenalidomide can also be prepared by taking the hydrated form of Lenalidomide in a solvent such as toluene, xylene or cyclohexane wherein the water in the product is completely separated by azeotropic distillation.

Also disclosed therein is polymorphic Form-B and its process for preparation comprising reacting polymorphic Form I with molar equivalent of hydrochloric acid and dissolving in water; adding activated charcoal to the solution, filtering, neutralizing and adjusting the pH to 7.5 to 8.0 with a suitable base to get the Lenalidomide precipitated followed by washing and drying under vacuum at temperature 65° C. to 110° C.

Amorphous Lenalidomide is disclosed in PCT publication No. WO 2009/114601.

PCT publication No. WO 2010/056384 discloses N,N-dimethylformamide solvate and dimethylsulfoxide solvate of Lenalidomide.

Anhydrous crystalline Form of Lenalidomide is disclosed in PCT publication No. WO 2010/061209. The process includes dissolving Lenalidomide in a solvent selected from the group comprising straight chained or branched C1-C5 alcohols, aliphatic ketones, and cyclic ethers or mixtures thereof and isolating the resultant crystalline solid. The publication also disclosed a process for conversion of anhydrous crystalline Form of Lenalidomide into prior art Lenalidomide crystalline form B (as disclosed in WO 2005/023192) comprising the steps of: (a) dissolving or suspending the anhydrous crystalline form in a mixture of a polar organic solvent and water; (b) causing the desired Form B to precipitate from the solution or suspension in step (a); and (c) isolating the solid crystalline Form.

WO2011061611 relates to process for preparation of polymorphic Form B of Lenalidomide which includes reducing 1-oxo-2-(2,6-dioxopiperidin-3-yl)-4-nitroisoindoline with Pd/C in N,N-dimethylformamide to obtain a N,N-dimethylformamide solvate of Lenalidomide; treating the N,N-dimethylformamide solvate of Lenalidomide so obtained with water; and isolating polymorphic Form B of Lenalidomide from the reaction mixture thereof.

In view of the above, there remains a need in the art to provide an improved process for synthesis of Lenalidomide which is efficient and industrially preferable.

Further, it is well known that poor solubility of an API can affect its bioavailability thereby affecting the dosage size in a pharmaceutical formulation. Since the polymorphic forms disclosed in the prior art are susceptible to conversion in an aqueous environment which is undesirable in terms of stability and storage capacity, the present inventors felt a need to provide more stable polymorphic Forms of Lenalidomide which has stability upon storage and during manufacture and in the presence of water and other aqueous solvent systems with desirable aqueous solubility.

It is therefore the other object of the invention to provide an improved method for preparation of Lenalidomide polymorphic Form B and Form I and to the process for conversion of polymorphic Form B to polymorphic Form I.

SUMMARY OF THE INVENTION

In an aspect, the present invention provides an efficient, industrially viable process for preparation of Lenalidomide comprising;

Brominating methyl 2-methyl-3-nitrobenzoate with NBS or 1,3-Dibromo-5,5-dimethylhydantoin in presence of AIBN in acetonitrile at a temperature in the range of 55-75° C. to isolate methyl 2-(bromomethyl)-3-nitrobenzoate (II);

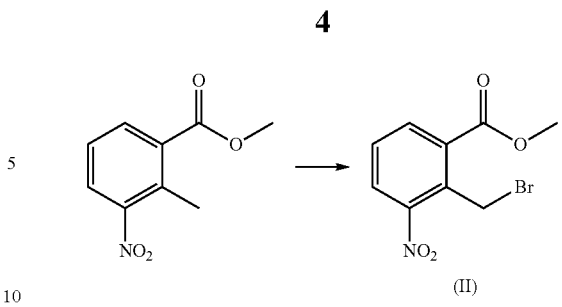

Condensing methyl 2-(bromomethyl)-3-nitrobenzoate (II) with 3-aminopiperidine-2,6-dione hydrochloride (III) in DMSO and a base at a temperature in the range of 50-55° C. to obtain 3-(4-nitro-1-oxoisoindolin-2-yl)piperidine-2,6-dione (IV);

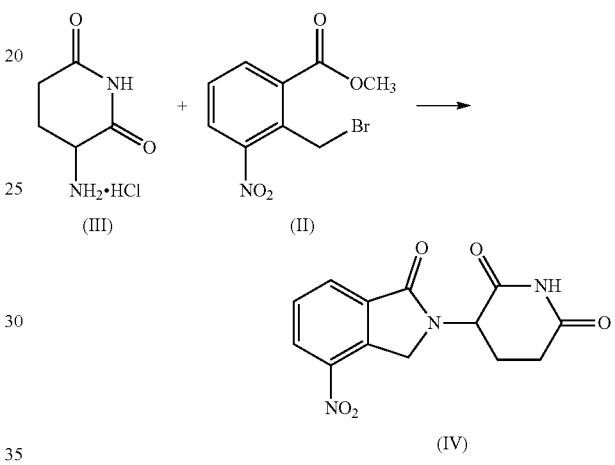

Hydrogenating 3-(4-nitro-1-oxoisoindolin-2-yl)piperidine-2,6-dione(IV) catalytically using 10% Pd/C under hydrogen atmosphere at 60-100 psi for about 6-12 hours in ammonia bubbled NMP or in a solvent mixture of aqueous ammonia and NMP to obtain crude 3-(4-amino-1-oxoisoindolin-2-yl) piperidine-2,6-dione (Lenalidomide);

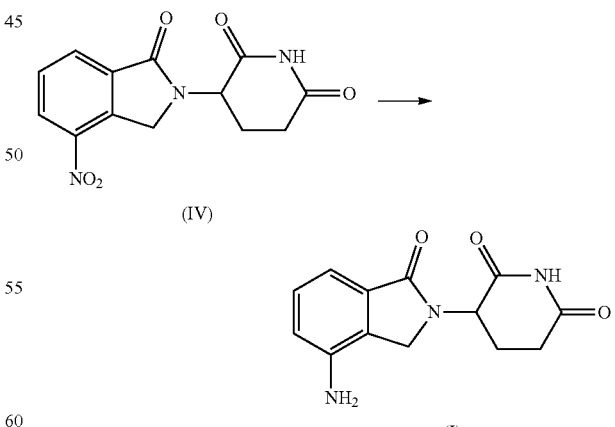

Dissolving the crude mass of step (iii) in acetone and refluxing followed by recrystallizing with charcoal treatment in a mixture of water and IPA in 1:2 ratio, at a temperature of about 100° C., to obtain pure 3-(4-amino-1-oxoisoindolin-2-yl)piperidine-2,6-dione (Lenalidomide).

In an aspect, the compound methyl 2-methyl-3-nitrobenzoate (II) was obtained by esterifying 2-methyl-3-nitrobenzoic acid with a methylating agent selected from dimethyl sulphate, diazomethane, dimethyl dicarbonate and the like in presence of a base selected from organic or inorganic base and a polar solvent at ambient temperature.

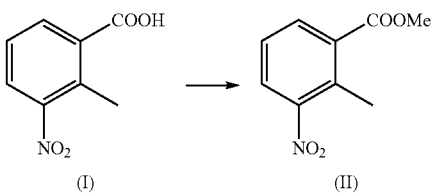

In yet another aspect, the purification of crude Lenalidomide was performed using acetone followed by recrystallization with charcoal tratment using IPA and water in a 2:1 ratio at a suitable temperature. The pure wet Lenalidomide can be converted to Form B or Form I by varying the temperature and extent of drying of wet Lenalidomide.

In another aspect, the present invention provides a process for preparation of Lenalidomide polymorph Form B, comprising heating purified wet Lenalidomide, obtained by the process of the present invention, in an oven to a temperature in the range of 65-70° C. for 4-6 hrs till moisture content of 3-4% was achieved.

In yet another aspect, the present invention provides a process for preparation of Lenalidomide polymorph Form I from polymorph Form B of the instant invention comprising drying the polymorph Form B in an oven at a temperature of 110-115° C. for 24-26 hours until the moisture content was less than 0.5%.

The polymorphs Form B and Form I were characterized by PXRD (FIGS. 1 and 2) and the PXRD data was observed to be similar to the PXRD peaks of Form B and Form I of U.S. Pat. No. 7,465,800 (US2005096351A1) and U.S. Pat. No. 8,877,932 (US20130059889) respectively.

DETAILED DESCRIPTION OF THE INVENTION

Figure 1:
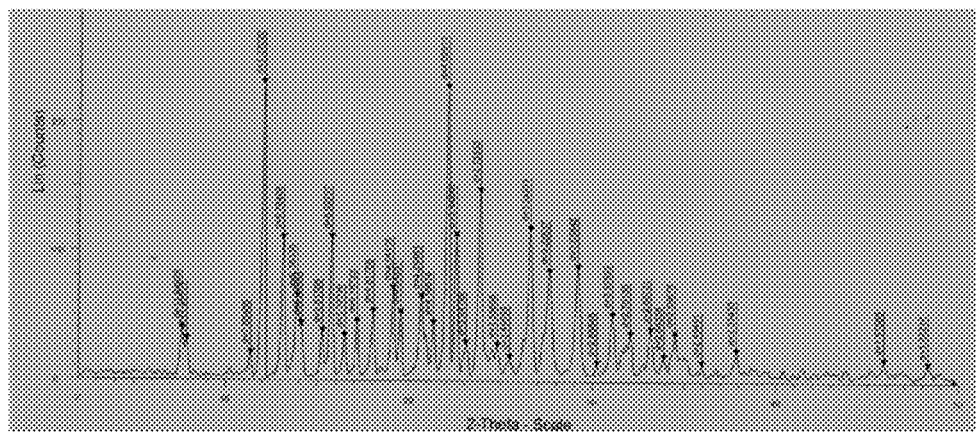
FIG. 1 relates to PXRD data of Lenalidomide Form B
FIG. 2 relates to PXRD data of Lenalidomide Form I

The present invention describes an efficient, industrially feasible process for preparation of Lenalidomide and its polymorphic Forms in good yield and purity.

Accordingly, the process for preparation of Lenalidomide comprises the following steps:

Step i:
Methyl 2-methyl-3-nitrobenzoate was brominated with a brominating agent selected from NBS or 1,3-Dibromo-5,5-dimethylhydantoin, preferably 1,3-Dibromo-5,5-dimethylhydantoin in acetonitrile followed by addition of azobisisobutyronitrile (AIBN). The reaction mixture was heated to a temperature in the range of 55-75° C. for about 12-15 hours. The progress of the reaction was monitored by TLC and HPLC and upon completion of the reaction, acetonitrile was concentrated (~80%) under vacuum to obtain crude compound. Water was added to crude, and the remaining acetonitrile was removed and the mixture was stirred at room temperature for 30 min. The solid was filtered, washed with water and stirred with isopropyl alcohol at room temperature for about 30 min which was again filtered and dried at room temperature to yield methyl 2-(bromomethyl)-3-nitrobenzoate (II).

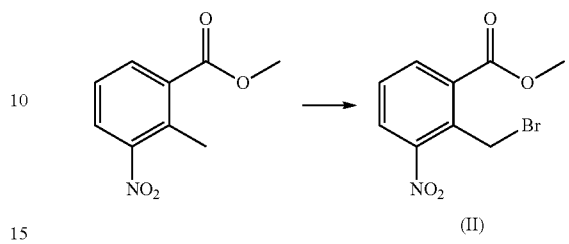

Step ii:
The coupling reaction comprises condensing methyl 2-(bromomethyl)-3-nitrobenzoate (II) with 3-aminopiperidine-2,6-dione hydrochloride (III) in DMSO. Accordingly, to the solution of 3-aminopiperidine-2,6-dione hydrochloride (III) in DMSO base selected from ethylamine, triethylamine, pyridine and the like; preferably triethylamine was added slowly under nitrogen over a period of 10 min. This was followed by addition of methyl 2-(bromomethyl)-3-nitrobenzoate (II) in DMSO under nitrogen over a period of 20 min and heated to 50-55° C. for 12 hrs. The progress of the reaction was monitored by HPLC and after completion, the reaction mixture was cooled to room temperature and water was added and heated to 50-55° C. for about 1 hr. The mixture was cooled to room temperature and filtered to get crude product. Methanol was added to the crude and stirred at 50° C. for 30 min, cooled to room temperature and filtered. The solid bed was further washed with methanol to yield 3-(4-nitro-1-oxoisoindolin-2-yl)piperidine-2,6-dione (IV).

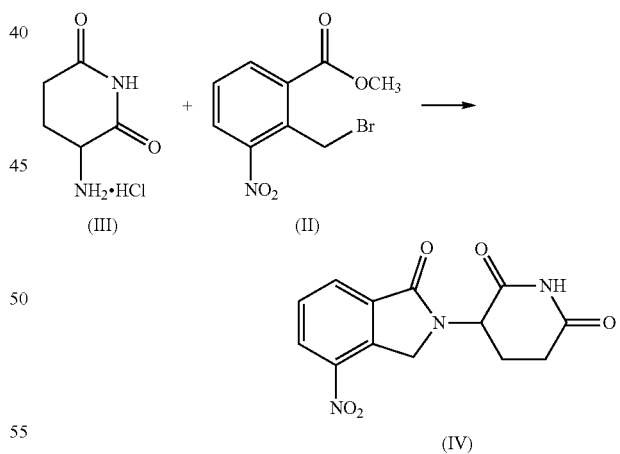

Step iii:
The reduction process comprises catalytic hydrogenation of 3-(4-nitro-1-oxoisoindolin-2-yl)piperidine-2,6-dione (IV) using 10% Pd/C under hydrogen atmosphere at a pressure of 60-100 psi for about 6-12 hours in ammonia bubbled NMP (N-methyl pyrrolidine) After completion of the reaction as indicated by HPLC the catalyst was filtered through celite bed and the bed was washed with NMP. The solvent was distilled using high vacuum and the reaction mixture was cooled to room temperature. Acetone was added to the reaction mixture and stirred at reflux for about an hour, cooled to room temperature and further stirred overnight. The solid formed was filtered, washed with acetone and suck dried to give crude 3-(4-amino-1-oxoisoindolin-2-yl)piperidine-2,6-dione (Lenalidomide).

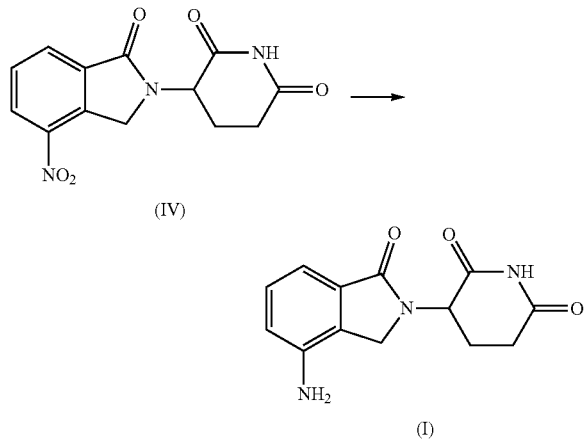

Alternately, the catalytic hydrogenation of 3-(4-nitro-1-oxoisoindolin-2-yl) piperidine-2,6-dione (IV) using 10% of Pd/C under hydrogen atmosphere at a pressure of 60-100 psi for about 6-12 hours can be performed using a mixture of aqueous ammonia and NMP as solvents. After completion of the reaction as indicated by HPLC, the catalyst was removed by filtration through celite bed and the bed was washed with NMP. The solvent was distilled using high vacuum and the reaction mixture was cooled to room temperature. Acetone was added to the reaction mixture and stirred at reflux for about an hour, cooled to room temperature and further stirred overnight. The solid formed was filtered, washed with acetone and suck dried to give crude 3-(4-amino-1-oxoisoindolin-2-yl)piperidine-2,6-dione (Lenalidomide).

Step iv:

Crude 3-(4-amino-1-oxoisoindolin-2-yl)piperidine-2,6-dione (Lenalidomide) of step (iii) was dissolved in acetone, stirred and refluxed for about an hour. The reaction mixture was cooled to room temperature and stirred overnight for about 15-18 hours. The solid was filtered, washed with acetone and suck dried to obtain crude mass. The crude mass was further recrystallized in a mixture of water:IPA in 1:2 ratio at a temperature of 85-90° C. This was followed by adding charcoal, stirring and filtering the hot solution through celite bed and washing the bed with water:IPA in a 1:2 ratio. The combined filtrates were distilled when almost 75% of the solvent was removed. The reaction mixture was cooled to room temperature; the solid was filtered to obtain pure wet Lenalidomide.

In an embodiment, the compound methyl 2-methyl-3-nitrobenzoate (II) was obtained by esterifying 2-methyl-3-nitrobenzoic acid with a methylating agent selected from dimethyl sulphate, diazomethane, dimethyl dicarbonate and the like in presence of a base selected from organic or inorganic base and a polar solvent at ambient temperature.

In an embodiment, the wet Lenalidomide obtained was dried at varying temperature and time to obtain the polymorphic Form B and Form I respectively.

Accordingly, the present invention discloses a process for preparation of Lenalidomide polymorph Form B, comprising heating purified wet Lenalidomide, obtained by the process of the present invention, in an oven to a temperature in the range of 65-70° C. for 4-6 hrs till moisture content 3-4% was achieved.

In yet another embodiment, the present invention discloses a process for preparation of Lenalidomide polymorph Form I from polymorph Form B, obtained by the present process, comprising drying the polymorph Form B in an oven at a temperature of 110-115° C. for 24-26 hours until the moisture content was less than 0.5%.

The polymorphs Form B and Form I were characterized by PXRD (FIGS. 1 and 2) and the PXRD data was observed to be similar to the PXRD peaks of Form B and Form I of U.S. Pat. No. 7,465,800 (US2005096351A1) and U.S. Pat. No. 8,877,932 (US20130059889) respectively.

While the present invention has been described in terms of its specific embodiments, certain modifications and equivalents will be apparent to those skilled in the art and are included within the scope of the invention. The examples included herein are provided to illustrate particular aspects of the disclosure and do not limit the scope of the present invention.

EXAMPLES

Example 1: Preparation of Methyl 2-methyl-3-nitrobenzoate

Mixture of 2-Methyl-3-nitrobenzoic acid (500 g, 2.76 mol) and dimethyl sulphate (365.54 g, 2.89 mol) was dissolved in acetone (5000 mL) and stirred at 25-30° C. for 10 min. Potassium carbonate (114.2 g) was added to the above reaction mixture at room temperature (25-30° C.) over a period of 60 min and stirred at ambient temperature for 30 min. Progress of the reaction was monitored by TLC/HPLC. On completion of reaction solid was filtered and washed with acetone (250 mL). Filtrate was concentrated on rotavpour. Obtained crude was diluted with DCM (2500 mL). Organic layer was washed with 2×1500 mL of water. The organic layer was concentrated on rotavpour to give the required product as pale yellow colored solid
Quantity of the product: 525.4 g
Yield: 97.53%
Purity: 99.9%, HPLC
MC (KF): 0.18%
Nature: Pale yellow solid.

Example 2: Preparation of methyl 2-(bromomethyl)-3-nitrobenzoate (II)

Methyl 2-methyl-3-nitrobenzoate (75 g, 0.38 mol) and acetonitrile (375 mL) were charged into 1 L three necked RBF. N-bromo succinimide (82.2 g, 0.46 mol) followed by azobisisobutyronitrile (7.5 g, 0.04 mol) was added to the reaction mixture and heated to 55-60° C. and maintained for 12 hrs. Progress of the reaction was monitored by TLC and HPLC. After the completion of reaction, acetonitrile was concentrated (~80%) under vacuum to obtain crude compound. Water (375 mL) was added to crude, remaining acetonitrile was removed and the mixture was stirred at room temperature for 30 min. The solid was filtered, washed with water (2×50 mL) and stirred with isopropyl alcohol (150 mL) at room temperature for 30 min which was again filtered and dried at room temperature.
Results:
Quantity of the product obtained: 89 g
Yield: 84.40%

Purity: (by HPLC) 98.17%

Nature: Light yellow colored solid

Example 3: Preparation of methyl 2-(bromomethyl)-3-nitrobenzoate (II)

Methyl 2-methyl-3-nitrobenzoate (25 g, 0.12 mol), AIBN (2.5 g, 10% w/w) and acetonitrile (125 mL) were charged into a 500 mL 3-neck RB flask and stirred at 25-30° C. for 15 min 1,3-Dibromo-5,5-dimethylhydantoin (21.98 g, 0.077 mol) was added to the above reaction mixture and heated at 68-72° C. for 6 hrs. The reaction mixture was concentrated, cooled to room temperature and diluted with water (125 mL). Obtained solid was filtered and washed with water (25 mL). The solid was stirred with IPA (125 mL) for 1 hr and filtered.

Results:

Quantity of the product obtained: 22.81 g

Yield: 64.97%

Purity: (by HPLC) 96.57%

Nature: Pale yellow solid

Example 4: Preparation of 3-(4-nitro-1-oxoisoindolin-2-yl)piperidine-2,6-dione (IV)

3-aminopiperidine-2,6-dione hydrochloride (III) (25 g, 0.15 mol) and dimethyl sulfoxide (150 mL) were charged into 500 mL 3N RBF. Triethylamine (62 g, 0.61 mol) was added slowly to the above reaction mixture under nitrogen over a period of 10 min. Methyl 2-(bromomethyl)-3-nitrobenzoate (II) (45.8 g, 0.16 mol) of example 3 dissolved in dimethyl sulfoxide (50 mL) was added to the reaction mixture under nitrogen over a period of 20 min and heated to 50-55° C. for 12 hrs. Progress of the reaction was monitored by HPLC. After the completion of the reaction, the reaction mixture was cooled to room temperature and water (250 mL) was added and heated to 55° C. for 1 hr. Then cooled to room temperature and filtered to get 42 g of crude. Methanol (125 mL) was added to the crude and stirred at 50° C. for 30 min, cooled to room temperature and filtered. The solid bed was washed with methanol (2×5 mL) to obtain the product.

Results:

Quantity of the product obtained: 34 g

Yield: 77.00%

Purity (by HPLC): 99.73%

Nature: grey colored solid

Example 5: Preparation of 3-(4-amino-1-oxoisoindolin-2-yl) piperidine-2,6-dione (Lenalidomide)

3-(4-nitro-1-oxoisoindolin-2-yl) piperidine-2,6-dione (IV) (2 kg, 6.91 mol) of example 4 was charged into 50 L Hydrogenation reactor. NH3 bubbled NMP (20 L) was charged. 10% Pd/C (100 g) was added and hydrogenation was carried for 12 hrs at hydrogen gas pressure of 60 psi. Progress of the reaction was monitored by HPLC. The catalyst was filtered through celite bed and bed was washed with NMP (2×2 L). The filtrate was concentrated at temperature 100° C. using high vacuum pump and the reaction mixture was cooled to room temperature. Acetone (60 mL) was added to the reaction mixture and stirred at reflux for one hour to obtain crude 3-(4-amino-1-oxoisoindolin-2-yl) piperidine-2,6-dione (Lenalidomide).

Results:

Quantity of the product obtained: 1.6 kg (crude)

Nature: Gray color solid

Example 6: Purification and recrystallization of crude 3-(4-amino-1-oxoisoindolin-2-yl) piperidine-2,6-dione To the crude compound (1.6 kg) of example 5 was added acetone in a reactor and the mixture was heated to 60-65° C. and further refluxed for 1 hour. The mixture was allowed to cool to room temperature and stirred overnight for about 16 hours. The reaction mass was filtered using Buchner funnel and the compound was washed with acetone (2 L) and suck dried for 1 hour to give pure 3-(4-amino-1-oxoisoindolin-2-yl)piperidine-2,6-dione (Lenalidomide).

The pure mass was then taken in water and IPA mixture in 1:2 ratio (96 L) and heated to 100° C. Charcoal (140 g) was added and stirred for 15 min. Filtered in hot condition and bed was washed with hot water and IPA mixture in 1:2 ratio (3 L). The solvent was distilled at 50° C. (~10 L solvent removed). Filtered (through Buckner funnel) and washed with IPA (2×1 L) then dried (HPLC showed 99.62% purity & 0.12% impurity). The reaction mixture was cooled to room temperature, the solid was filtered, washed with DM water and dried with suction to obtain pure wet Lenalidomide.

Results:

Quantity of the product obtained: 1.18 kg

Yield: 66.3%

Purity: (by HPLC) 99.84%

Nature: Off-white solid

Example 7: Preparation of 3-(4-amino-1-oxoisoindolin-2-yl) piperidine-2,6-dione (Lenalidomide Form B)

3-(4-nitro-1-oxoisoindolin-2-yl) piperidine-2,6-dione (IV) (60 g. 0.207 mol) and NMP (400 mL) were charged into 1 L Hydrogenation flask. To the reaction mixture 10% Pd/C (12 g) in NMP (140 mL) followed by aq. ammonia (30 mL) was added and subjected for hydrogenation at 60-100 psi-hydrogen pressure for 6-12 hrs. Progress of the reaction was monitored by HPLC. The catalyst was filtered through celite and washed with NMP (180 mL). Around 690 mL of NMP was distilled using high vacuum. Reaction mixture was cooled to room temperature acetone (600 mL) was added and stirred at reflux for 1 hr. The Reaction mixture was cooled to room temperature and stirred for overnight (~16 hr). Solid was filtered, washed with acetone (60 mL) and dried with suction to get crude Lenalidomide (~40.2 g), The crude Lenalidomide (40.2 g) was taken in Water:IPA, 1:2 (1800 mL) and the mixture was heated to reflux at 85-90° C. Charcoal (Darco) (12 g) was added, stirred for 15 min and filtered hot through celite and washed with water: IPA, 1:2 (180 mL). The combined filtrate was distilled. The distillation was stopped when almost 75% of the solvent was removed. The reaction mixture was cooled to room temperature and solid was filtered, washed with IPA (30 mL) dried with suction to yield pure wet Lenalidomide (35.2 g), Obtained product was heated in an oven at 65-70° C. for 4-6 hrs till moisture of the product reduced to 3-4%. PXRD confirmed the product as Form B. (FIG. 1).

Results:
Quantity of the product obtained: 34.4 g
Yield: 62.53%
Nature: Light yellow colored solid Example 8: Preparation of 3-(4-amino-1-oxoisoindolin-2-yl) piperidine-2,6-dione (Lenalidomide Form I)

Figure 2:
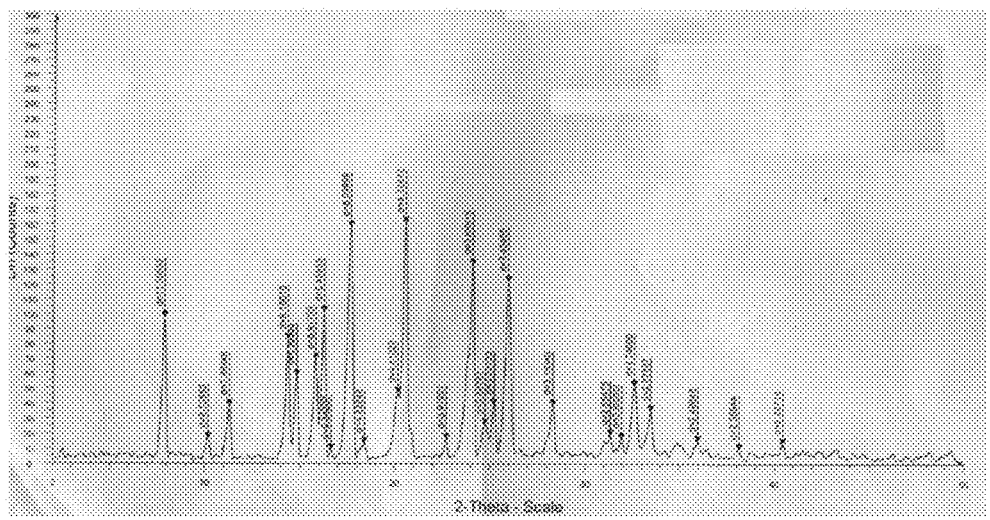

3-(4-nitro-1-oxoisoindolin-2-yl) piperidine-2,6-dione (IV) (60 g. 0.207 mol) and NMP (400 mL) were charged into 1 L hydrogenation flask. To the reaction mixture 10% of Pd/C (12 g) in NMP (140 mL) followed by aq. ammonia (30 mL) was added and subjected for hydrogenation at 60-100 psi-hydrogen pressure for 6-12 hrs. Progress of the reaction was monitored by HPLC. The catalyst was filtered through celite and washed with NMP (180 mL). Around 690 mL of NMP was distilled using high vacuum. Reaction mixture was cooled to room temperature Acetone (600 mL) was added and stirred at reflux for 1 hr. The Reaction mixture was cooled to room temperature and stirred for overnight (~16 hr). Solid was filtered, washed with acetone (60 mL) and dried with suction to get crude-41 g, To the 41 g-crude, acetone (600 mL) and NMP (30 mL) was added and stirred at reflux for 1 hr. The reaction mixture was cooled to room temperature; solid was filtered, washed with Acetone (30 mL) and dried with suction to get crude-37 g. The crude 37 g was taken in Water:IPA, 1:2 (1800 mL) and the mixture was heated to reflux at 85-90° C. Charcoal (Darco) (12 gm) was added, stirred for 15 min and filtered hot through celite and washed with Water:IPA, 1:2 (180 mL). The combined filtrate was distilled. The distillation was stopped when almost 75% of the solvent was removed. The reaction mixture was cooled to room temperature and solid was filtered, washed with IPA (30 mL) dried with suction to yield pure Lenalidomide-34.2 g, Obtained product was heated in oven at 65-70° C. for 4-6 hrs till moisture of the product reduced to 3-4%. The product was further dried in oven at 110-115° C. for 24-26 hrs. Loss on drying of the material was less than 0.5%. PXRD confirmed the product as Form I. (FIG. 2).

Results:
Quantity of the product obtained: 34.2 g
Yield: 63.6%
Nature: Light yellow colored solid

We claim:
1. A process for preparation of Lenalidomide, comprising;
   i. Brominating methyl 2-methyl-3-nitrobenzoate with NBS or 1,3-Dibromo-5,5-dimethyl-hydantoin in presence of AIBN in acetonitrile at a temperature in the range of 55-75° C. to isolate methyl 2-(bromomethyl)-3-nitrobenzoate (II);

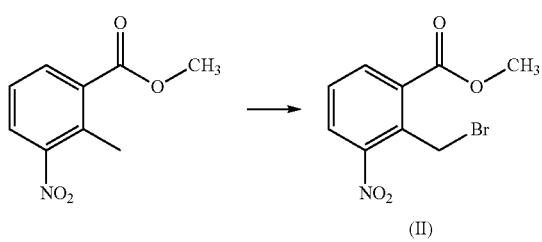

ii. Condensing methyl 2-(bromomethyl)-3-nitrobenzoate (II) with 3-amino-piperidine-2,6-dione hydrochloride (III) in DMSO and a base at a temperature in the range of 50-55° C. to obtain 3-(4-nitro-1-oxoisoindolin-2-yl) piperidine-2,6-dione (IV);

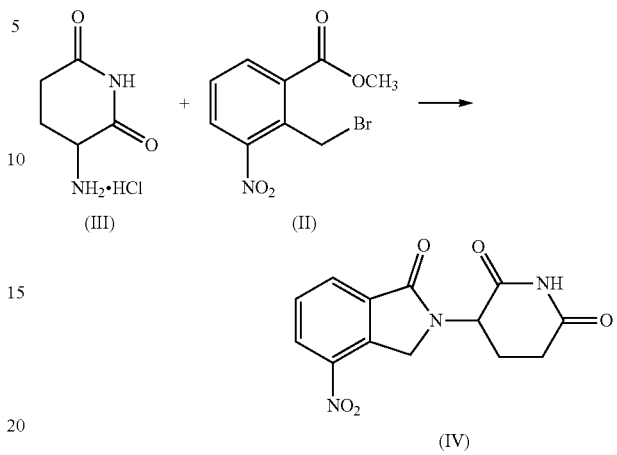

iii. hydrogenating 3-(4-nitro-1-oxoisoindolin-2-yl)piperidine-2,6-dione (IV) catalytically using 10% Pd/C under hydrogen atmosphere at 60-100 psi for about 6-12 hours in ammonia bubbled NMP or in a solvent mixture of aqueous ammonia and NMP to obtain crude 3-(4-amino-1-oxoisoindolin-2-yl)piperidine-2,6-dione (Lenalidomide);

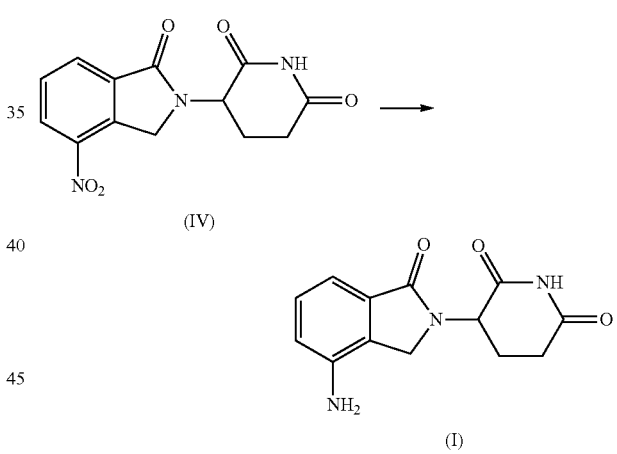

iv. Dissolving the crude mass of step (iii) in acetone and refluxing to obtain pure Lenalidomide followed by recrystallizing from the mixture of water and IPA in 1:2 ratio at a temperature of about 100° C. to obtain pure wet 3-(4-amino-1-oxoisoindolin-2-yl)piperidine-2,6-dione (Lenalidomide).

2. The process according to claim 1, wherein the brominating agent used in step (i) is 1,3-Dibromo-5,5-dimethylhydantoin.

3. The process according to claim 1, wherein, methyl 2-methyl-3-nitrobenzoate (II) is prepared by esterifying 2-methyl-3-nitrobenzoic acid with a methylating agent in presence of a base and a polar solvent at ambient temperature.

4. The process according to claim 1, wherein the brominating agent used in step (i) is NBS.

* * * * *